US010669302B2

(12) United States Patent
Yang et al.

(10) Patent No.: US 10,669,302 B2
(45) Date of Patent: Jun. 2, 2020

(54) CRYSTAL FORM OF FLUDARABINE PHOSPHATE, PREPARATION METHOD THEREFOR, AND APPLICATION THEREOF

(71) Applicant: Zhejiang Hisun Pharmaceutical Co., Ltd., Zhejiang (CN)

(72) Inventors: Zhiqing Yang, Zhejiang (CN); Liang Zhang, Zhejiang (CN); Xiangyang Zhang, Zhejiang (CN); Zhenjuan Shi, Zhejiang (CN); Di Su, Zhejiang (CN); Hongying Luo, Zhejiang (CN); Dejin Fu, Zhejiang (CN)

(73) Assignee: ZHEJIANF HISUN PHARMACEUTICAL CO., LTD., Zhejiang (CN)

( * ) Notice: Subject to any disclaimer, the term of this patent is extended or adjusted under 35 U.S.C. 154(b) by 0 days.

(21) Appl. No.: 15/755,618

(22) PCT Filed: Aug. 26, 2016

(86) PCT No.: PCT/CN2016/096878
§ 371 (c)(1),
(2) Date: Feb. 27, 2018

(87) PCT Pub. No.: WO2017/036356
PCT Pub. Date: Mar. 9, 2017

(65) Prior Publication Data
US 2018/0244711 A1 Aug. 30, 2018
US 2019/0112327 A2 Apr. 18, 2019

(30) Foreign Application Priority Data

Aug. 28, 2015 (CN) .......................... 2015 1 0540739

(51) Int. Cl.
*C07H 19/20* (2006.01)
*C07H 1/06* (2006.01)

(52) U.S. Cl.
CPC ............... *C07H 19/20* (2013.01); *C07H 1/06* (2013.01); *C07B 2200/13* (2013.01)

(58) Field of Classification Search
CPC .................................. C07H 19/20; C07H 1/06
See application file for complete search history.

(56) References Cited

U.S. PATENT DOCUMENTS

| 2003/0176391 A1* | 9/2003 | Heil ...................... A61K 9/2018 514/48 |
| 2006/0240529 A1 | 10/2006 | Farina et al. |
| 2011/0201675 A1* | 8/2011 | Jimeno ................ A61K 31/192 514/44 R |

FOREIGN PATENT DOCUMENTS

| CN | 103040855 A | 4/2013 |
| CN | 104592337 A | 5/2015 |
| EP | 1464708 A1 | 10/2004 |
| WO | 2004087939 A1 | 10/2004 |
| WO | 2007144168 A1 | 12/2007 |

OTHER PUBLICATIONS

Google machine translation of CN 103040855, https://patents.google.com/patent/CN103040855B/en?og=103040855, accessed online on Mar. 29, 2019. (Year: 2019).*
International Search Report issued in connection with International Application No. PCT/CN2016/096878 dated Nov. 17, 2016, 4 pages.
Caira, M. R. 1998. Crystalline Polymorphism of Organic Compounds. vol. 198, pp. 163-208.
Extended European Search Report for EP Application No. 16840785, dated Apr. 29, 2019, 8 pages.

* cited by examiner

*Primary Examiner* — Jonathan S Lau
(74) *Attorney, Agent, or Firm* — Armstrong Teasdale LLP

(57) ABSTRACT

Provided are a new crystal form of fludarabine phosphate, a preparation method therefor, a pharmaceutical composition containing same, and an application thereof in preparing medicine. Crystal forms I and II of the fludarabine phosphate have excellent properties in terms of solubleness, dissolution rate, chemical stability, and processing adaptability.

10 Claims, 8 Drawing Sheets

CRYSTAL FORM OF FLUDARABINE PHOSPHATE, PREPARATION METHOD THEREFOR, AND APPLICATION THEREOF

This application claims priority to International Patent Application No. PCT/CN2016/096878, filed on Aug. 26, 2016, which claims priority to CN Patent Application No. 201510540739.6, filed on Aug. 28, 2015, the disclosures of which are hereby expressly incorporated by reference in their entireties.

TECHNICAL FIELD

The present invention relates to the field of chemical pharmacy. More specifically, the present invention relates to novel crystal forms of fludarabine phosphate and preparation methods thereof, pharmaceutical compositions comprising the crystal forms and an application thereof in preparing medicines.

TECHNICAL BACKGROUND

Fludarabine phosphate is a fluorinated nucleotide analog of the antiviral drug vidarabine that is relatively resistant to the deamination of adenosine deaminase and is generally used in the treatment of chronic lymphocytic leukemia, it can be rapidly dephosphorylated to 2F-ara-A in human body, and 2F-ara-A can be taken up by cells and then it becomes an active triphosphate 2F-ara-ATP after being phosphorylated by intracellular deoxycytidine kinase. The metabolite can inhibit the synthesis of DNA by inhibiting nucleotide reductase, DNA polymerase α, δ and ε, DNA primase and DNA ligase. In addition, RNA polymerase II can also be partially inhibited to reduce the synthesis of protein.

The chemical name of fludarabine phosphate is: 9-β-D-arabinofuranosyl-2-fluoroadenine-5'-phosphate, the structural formula is as follows:

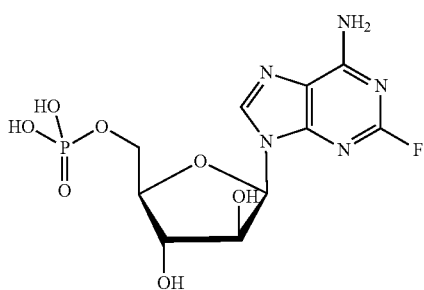

For polymorphic drugs, different crystal forms can have different physical and chemical properties, including melting point, chemical stability, apparent solubility, dissolution rate, optical and mechanical properties etc. These physicochemical properties directly determine whether a specific crystal form can prepare pharmaceutical preparations, and affect the quality of APIs and preparations. Therefore, for pharmaceutical formulations, it is essential to develop new crystal forms with excellent solubility and dissolution rates to meet the demanding requirements of pharmaceuticals.

SUMMARY OF THE INVENTION

One of the objects of the present invention is to provide novel crystal forms of fludarabine phosphate. In the present invention they are named as crystal forms I and II of fludarabine phosphate.

Crystal form I of fludarabine phosphate of the present invention has good chemical and physical stability and excellent properties in terms of solubility and dissolution rate.

The X-ray powder diffraction pattern of crystal form I of fludarabine phosphate of the present invention has characteristic peaks at 2θ (°) values of 9.1±0.2, 17.3±0.2, 18.1±0.2, 20.4±0.2, 23.0±0.2, 28.1±0.2.

Furthermore, the X-ray powder diffraction pattern of crystal form I of fludarabine phosphate also has characteristic peaks at 2θ (°) values of 6.2±0.2, 10.5±0.2, 12.3±0.2, 18.9±0.2, 26.3±0.2.

Furthermore, the X-ray powder diffraction pattern of crystal form I of fludarabine phosphate of the present invention has 2θ, d and relative intensity data as shown in Table 1 below:

TABLE 1

| Peak No. | 2θ (°) | d (Å) | Relative intensity (%) |
|---|---|---|---|
| 1 | 6.2 | 14.2 | 1.7 |
| 2 | 9.1 | 9.8 | 38.4 |
| 3 | 10.5 | 8.5 | 1.0 |
| 4 | 12.3 | 7.2 | 1.6 |
| 5 | 17.3 | 5.1 | 100 |
| 6 | 18.1 | 4.9 | 25.6 |
| 7 | 18.9 | 4.7 | 2.5 |
| 8 | 20.4 | 4.4 | 7.5 |
| 9 | 23.0 | 3.9 | 8.1 |
| 10 | 26.3 | 3.4 | 4.3 |
| 11 | 28.1 | 3.2 | 4.8 |

The X-ray powder diffraction pattern of crystal form II of fludarabine phosphate of the present invention has characteristic peaks at 2θ (°) values of 10.6±0.2, 16.8±0.2, 17.7±0.2, 18.6±0.2, 19.0±0.2, 22.8±0.2, 24.5±0.2, 25.9±0.2, 26.9±0.2, 28.4±0.2.

Furthermore, the X-ray powder diffraction pattern of crystal form II of fludarabine phosphate also has characteristic peaks at 2θ (°) values of 6.6±0.2, 8.9±0.2, 13.0±0.2, 13.3±0.2, 15.6±0.2, 20.7±0.2, 21.2±0.2, 21.6±0.2.

Furthermore, the X-ray powder diffraction pattern of crystal form II of fludarabine phosphate of the present invention has 2θ, d and relative intensity data as shown in Table 2 below:

TABLE 2

| Peak No. | 2θ (°) | d (Å) | Relative intensity (%) |
|---|---|---|---|
| 1 | 6.6 | 13.3 | 5.6 |
| 2 | 8.9 | 9.9 | 7.5 |
| 3 | 10.6 | 8.3 | 13.1 |
| 4 | 13.0 | 6.8 | 4.3 |
| 5 | 13.3 | 6.6 | 4.8 |
| 6 | 15.6 | 5.7 | 9.8 |
| 7 | 16.8 | 5.3 | 90.3 |
| 8 | 17.7 | 5.0 | 100 |
| 9 | 18.6 | 4.8 | 64.5 |
| 10 | 19.0 | 4.7 | 31.9 |
| 11 | 20.7 | 4.3 | 8.0 |
| 12 | 21.2 | 4.2 | 9.3 |
| 13 | 21.6 | 4.1 | 14.0 |
| 14 | 22.8 | 3.9 | 36.2 |
| 15 | 24.5 | 3.6 | 21.7 |
| 16 | 25.9 | 3.4 | 23.8 |
| 17 | 26.9 | 3.3 | 38.2 |
| 18 | 28.4 | 3.1 | 18.3 |

Unrestrictedly, in an embodiment of the present invention, crystal form I of fludarabine phosphate has an X-ray powder diffraction pattern as shown in FIG. 1.

Unrestrictedly, in an embodiment of the present invention, crystal form II of fludarabine phosphate has an X-ray powder diffraction pattern as shown in FIG. 5.

In addition, crystal form I of fludarabine phosphate of the present invention can be characterized by the infrared absorption spectrum measured by KBr pellet, it has characteristic peaks at about 3540.98 cm, 3441.94 cm$^{-1}$, 3281.29 cm$^{-1}$, 3132.67 cm$^{-1}$, 2926.87 cm$^{-1}$, 1931.71 cm$^{-1}$, 1852.15 cm$^{-1}$, 1660.11 cm$^{-1}$, 1608.04 cm$^{-1}$, 1513.16 cm$^{-1}$, 1495.86 cm$^{-1}$, 1398.34 cm$^{-1}$, 1373.15 cm$^{-1}$, 1300.04 cm$^{-1}$, 1285.26 cm$^{-1}$, 1195.97 cm$^{-1}$, 1141.17 cm$^{-1}$, 1127.75 cm$^{-1}$, 1060.68 cm$^{-1}$, 965.47 cm$^{-1}$, 945.37 cm$^{-1}$, 885.22 cm$^{-1}$, 846.24 cm$^{-1}$, 826.56 cm$^{-1}$, 796.89 cm$^{-1}$, 730.71 cm$^{-1}$, 549.96 cm$^{-1}$, 499.45 cm$^{-1}$.

Furthermore, the infrared absorption spectrum of crystal form I of fludarabine phosphate has characteristic peaks at about 3540.98 cm$^{-1}$, 3441.94 cm$^{-1}$, 3281.29 cm$^{-1}$, 3132.67 cm$^{-1}$, 3066.58 cm$^{-1}$, 2926.87 cm$^{1L}$, 2724.39 cm$^{-1}$, 2600.84 cm$^{-1}$, 1931.71 cm$^{-1}$, 1852.15 cm$^{-1}$, 1660.11 cm$^{-1}$, 1608.04 cm$^{-1}$, 1540.43 cm$^{-1}$, 1513.16 cm$^{-1}$, 1495.86 cm$^{-1}$, 1457.23 cm$^{-1}$, 1433.19 cm$^{-1}$, 1398.34 cm$^{-1}$, 1373.15 cm$^{-1}$, 1358.21 cm$^{-1}$, 1332.69 cm$^{-1}$, 1300.04 cm$^{-1}$, 1285.26 cm$^{-1}$, 1195.97 cm$^{-1}$, 1141.17 cm$^{-1}$, 1127.75 cm$^{-1}$, 1060.68 cm$^{-1}$, 965.47 cm$^{-1}$, 945.37 cm$^{-1}$, 885.22 cm$^{-1}$, 846.24 cm$^{-1}$, 826.56 cm$^{-1}$, 796.89 cm$^{-1}$, 783.23 cm$^{-1}$, 730.71 cm$^{-1}$, 681.62 cm$^{-1}$, 660.75 cm$^{-1}$, 648.10 cm$^{-1}$, 602.85 cm$^{-1}$, 586.69 cm$^{-1}$, 549.96 cm$^{-1}$, 515.78 cm$^{-1}$, 499.45 cm-1, 413.43 cm$^{-1}$.

Crystal form II of fludarabine phosphate of the present invention can be characterized by the infrared absorption spectrum measured by KBr pellet, it has characteristic peaks at about 3441.51 cm$^{-1}$, 3325.76 cm$^{-1}$, 3132.36 cm$^{-1}$, 2941.82 cm$^{-1}$, 2926.71 cm$^{-1}$, 1929.91 cm$^{-1}$, 1846.75 cm$^{-1}$, 1775.06 cm$^{-1}$, 1661.24 cm$^{-1}$, 1613.12 cm$^{-1}$, 1591.32 cm$^{-1}$, 1515.42 cm$^{-1}$, 1491.96 cm$^{-1}$, 1458.79 cm$^{-1}$, 1409.93 cm$^{-1}$, 1398.40 cm$^{-1}$, 1370.40 cm$^{-1}$, 1324.81 cm$^{-1}$, 1292.64 cm$^{-1}$, 1211.73 cm$^{-1}$, 971.33 cm$^{-1}$, 938.68 cm$^{-1}$, 890.69 cm$^{-1}$, 846.62 cm$^{-1}$, 825.55 cm$^{-1}$, 791.88 cm$^{-1}$, 731.43 cm$^{-1}$, 650.66 cm$^{-1}$, 623.65 cm$^{-1}$, 603.28 cm$^{-1}$, 543.45 cm$^{-1}$, 548.31 cm$^{-1}$, 515.79 cm$^{-1}$, 495.10 cm$^{-1}$.

Furthermore, the infrared absorption spectrum of crystal form II of fludarabine phosphate has characteristic peaks at about 3441.51 cm$^{-1}$, 3325.76 cm$^{-1}$, 3189.72 cm$^{-1}$, 3132.36 cm$^{-1}$, 2941.82 cm$^{-1}$, 2926.71 cm$^{-1}$, 2602.04 cm$^{-1}$, 1929.91 cm$^{-1}$, 1846.75 cm$^{-1}$, 1775.06 cm$^{-1}$, 1661.24 cm$^{-1}$, 1613.12 cm$^{-1}$, 1591.32 cm$^{-1}$, 1515.42 cm$^{-1}$, 1491.96 cm$^{-1}$, 1458.79 cm$^{-1}$, 1432.16 cm$^{-1}$, 1409.93 cm$^{-1}$, 1398.40 cm$^{-1}$, 1370.40 cm$^{-1}$, 1324.81 cm$^{-1}$, 1292.64 cm$^{-1}$, 1272.87 cm$^{-1}$, 1211.73 cm$^{-1}$, 1140.84 cm$^{-1}$, 1056.29 cm$^{-1}$, 971.33 cm$^{-1}$, 938.68 cm$^{-1}$, 890.69 cm$^{-1}$, 846.62 cm$^{-1}$, 825.55 cm$^{-1}$, 791.88 cm$^{-1}$, 731.43 cm$^{-1}$, 683.29 cm$^{-1}$, 662.83 cm$^{-1}$, 650.66 cm$^{-1}$, 623.65 cm$^{-1}$, 603.28 cm$^{-1}$, 543.45 cm$^{-1}$, 548.31 cm$^{-1}$, 515.79 cm$^{-1}$, 495.10 cm$^{-1}$, 469.87 cm$^{-1}$, 4417.68 cm$^{-1}$.

Unrestrictedly, in an embodiment of the present invention, crystal form I of fludarabine phosphate has an infrared spectrum as shown in FIG. 2.

Unrestrictedly, in an embodiment of the present invention, crystal form II of fludarabine phosphate has an infrared spectrum as shown in FIG. 6.

The differential scanning calorimetry (DSC) pattern of crystal form I of fludarabine phosphate of the present invention has a dehydrate peak beginning at 65° C. and has an exothermic peak within the range of 212.8-219.8° C.

Crystal form I of fludarabine phosphate of the present invention is a monohydrate.

The melting point of crystal form I of fludarabine phosphate of the present invention is 207° C.

The melting point of crystal form II of fludarabine phosphate of the present invention is 195° C.

Unrestrictedly, crystal form I of fludarabine phosphate of the present invention has a DSC thermogram as shown in FIG. 3.

Unrestrictedly, crystal form I of fludarabine phosphate of the present invention has a TGA thermogram as shown in FIG. 4.

Unrestrictedly, crystal form II of fludarabine phosphate of the present invention has a DSC thermogram as shown in FIG. 7.

Unrestrictedly, crystal form II of fludarabine phosphate of the present invention has a TGA thermogram as shown in FIG. 8.

Another object of the present invention is to provide a preparation method for crystal form I of fludarabine phosphate, specifically, the method is as follows:

Method One (1) 9-β-D-arabinofuranosyl-2-fluoroadenine-5'-phosphate is added to an acidic aqueous solution;

(2) dissolved;

(3) the pH is adjusted with an alkaline solution, wherein the pH is less than 1.2, preferably in the pH range of 0-1.0;

(4) crystallized;

(5) filtered to obtain crystal form I of 9-β-D-arabinofuranosyl-2-fluoroadenine-5'-phosphate.

Method Two (1) 9-β-D-arabinofuranosyl-2-fluoroadenine-5'-phosphate is added to an alkaline aqueous solution;

(2) dissolved;

(3) the pH is adjusted with an acidic solution, wherein the pH is less than 1.2, preferably in the pH range of 0-1.0;

(4) crystallized;

(5) filtered to obtain crystal form I of 9-β-D-arabinofuranosyl-2-fluoroadenine-5'-phosphate.

Method Three (1) the fermentation broth containing 9-β-D-arabinofuranosyl-2-fluoroadenine-5'-phosphate is filtered;

(2) the filtrate is added to a crystallizer;

(3) the pH is adjusted with an acidic solution, wherein the pH is less than 1.2, preferably in the pH range of 0-1.0;

(4) crystallized;

(5) filtered to obtain crystal form I of 9-f-D-arabinofuranosyl-2-fluoroadenine-5'-phosphate.

Another object of the present invention is also to provide a preparation method for crystal form II of fludarabine phosphate, specifically, the method is as follows:

(1) take an acidic or alkaline solution with 9-β-D-arabinofuranosyl-2-fluoroadenine-5'-phosphate as the solute and water as the solvent;

(2) the pH is adjusted with an alkaline or acidic solution, wherein the pH is between 1.2 and 2.0;

(3) crystallized;

(4) filtered;

(5) the crystals are stirred in water and are filtered to give crystal form II of 9-β-D-arabinofuranosyl-2-fluoroadenine-5'-phosphate.

When an acidic aqueous solution or an alkaline aqueous solution is used as the solvent, the weight-to-volume ratio of fludarabine phosphate to the solvent is preferably 1:10-1:100 (g/ml), more preferably 1:15-1:50 (g/ml).

In the above Method One and Method Two, the unit of the weight-to-volume ratio of fludarabine phosphate to the corresponding solvent may be g/ml, Kg/L etc., depending on the specific operation scale. In said methods, the acidic solution used can be sulfuric acid, hydrochloric acid or phosphoric acid, etc., preferably a hydrochloric acid solution; the alkaline solution used may be sodium hydroxide, potassium hydroxide, sodium carbonate, sodium bicarbonate, potassium tert-butoxide, sodium methoxide, sodium ethoxide, etc., preferably sodium hydroxide.

The raw material of fludarabine phosphate used in the method of the present invention is commercially available or can be prepared according to known methods. There's no special limitation to the solvents used in the present invention, and the solvents can be conventional solvents that are commercially available.

In another aspect, the present invention also provides a pharmaceutical composition comprising a therapeutically effective amount of crystal form I of fludarabine phosphate as the active ingredient. Preferably, in the pharmaceutical composition, crystal form I of fludarabine phosphate may be mixed with one or more pharmaceutically acceptable solid or liquid diluents and/or excipients and the mixture can be made into pharmaceutical preparations, preferably injections and oral preparations.

In another aspect, the present invention also provides a pharmaceutical composition comprising a therapeutically effective amount of crystal form II of fludarabine phosphate as the active ingredient. Preferably, in the pharmaceutical composition, crystal form II of fludarabine phosphate may be mixed with one or more pharmaceutically acceptable solid or liquid diluents and/or excipients and the mixture can be made into pharmaceutical preparations, preferably injections and oral preparations.

The present invention further provides the use of crystal form I of fludarabine phosphate in the preparation of antitumor medicaments.

The present invention also provides the use of crystal form II of fludarabine phosphate in the preparation of antitumor medicaments.

Unless otherwise specified, the "stirring" in the method of the present invention can be carried out by conventional methods in the art, for example, stirring method includes magnetic stirring and mechanical stirring.

The X-ray powder diffraction apparatus and the test conditions involved in the present invention are: X-ray diffraction apparatus model Rigaku D/max-2200 Cu target; operation method: scanning speed 4°/min, scanning step width 0.01°.

The infrared spectrophotometer and the test conditions involved in the present invention are: infrared spectrophotometer model: BRWKER IECTOR 22; operation method: KBr pellet method, scanning range 400-4000 $cm^{-1}$.

The differential scanning calorimeter and the test conditions involved in the present invention are: differential scanning calorimeter model: NETZSCH DSC200 F3 Iaia; operation method: heating rate 10° C./min, temperature range: 30-250° C.

The thermogravimetric analyzer and the test conditions involved in the present invention are: thermogravimetric analyzer model: PerkinElmer TGA400; operation method: heating rate 10° C./min, temperature range: 30-300° C.

The melting point apparatus and the test conditions involved in the present invention are: melting point apparatus model: OptiMelt MPA100; operation method: heating rate 10° C./min, temperature range: 30-300° C.

The turbidimeter and the test conditions involved in the present invention are: turbidimeter model: MERCK TURBIQUANT 1500IR; operation method: the purified water was used as a zero point control, 50 mg of crystal form I of fludarabine phosphate and 50 mg of crystal form II of fludarabine phosphate were dissolved in 10 ml of purified water respectively as test samples, the specific test data can be seen in Table 3.

The liquid chromatography test conditions involved in the present invention are: chromatographic column: SHIMADZU, VP-ODS, 4.6 mm×15 cm 5 µm or equivalent;

mobile phase A: 10 mM monopotassium phosphate (0.01 mol/l):methanol=47:3; detection wavelength: 260 nm; flow rate: 1.0 ml/min; injection volume: 10 µl.

It should be emphasized that the meaning or the intended protection scope of the numerical values or numerical endpoints involved in the technical solutions of the present invention are not limited to the numbers themselves, and those skilled in the art should understand that they include those allowable ranges of errors that have been widely accepted in the art, such as experimental errors, measurement errors, statistical errors and random errors, and the ranges of these errors are all included in the scope of the present invention.

After an extensive study, the inventors of the present invention have found the crystal forms I and II of fludarabine phosphate, the crystal forms I and II have good solubility and have the advantages of high product purity, excellent physical and chemical properties, good chemical stability and reproducible processing (filtration, drying); while the crystallization process of the crystal forms I and II of fludarabine phosphate of the invention is simple, the crystallization solvent is water with the use of organic solvent avoided, the cost is greatly reduced, and the pollution to the environment is also reduced. And the crystallization process of the present invention is easy to operate, and the industrial production can be achieved. In addition, the crystal forms I and II of fludarabine phosphate of the present invention have good dissolution rates.

DETAILED DESCRIPTION OF THE INVENTION

The present invention will be further illustrated by the examples below, but it is not limited to these examples.

The raw material of fludarabine phosphate used in the method of the present invention can be prepared according to known methods, such as the method mentioned in the U.S. patent application US20060240529, or the method mentioned in the international patent application WO2007144168A1.

Example 1

10 g of fludarabine phosphate (HPLC purity>90%) was dissolved in 200 ml of aqueous hydrochloric acid solution, the temperature was controlled at 10-15° C., stirred continuously for 30 min, fludarabine phosphate was dissolved and obtain a solution of fludarabine phosphate; the solution was filtered and get clarified filtrate, saturated sodium hydroxide solution was added dropwise, pH=1.0, and crystallization was carried out under 25° C. while stirring for 8 h, the solution was filtered and dried under vacuum at 20° C., 7.1 g crystals were obtained, the purity was 99.8% by HPLC, the crystals were confirmed to be crystal form I by X-ray powder diffraction detection.

Figure 1:
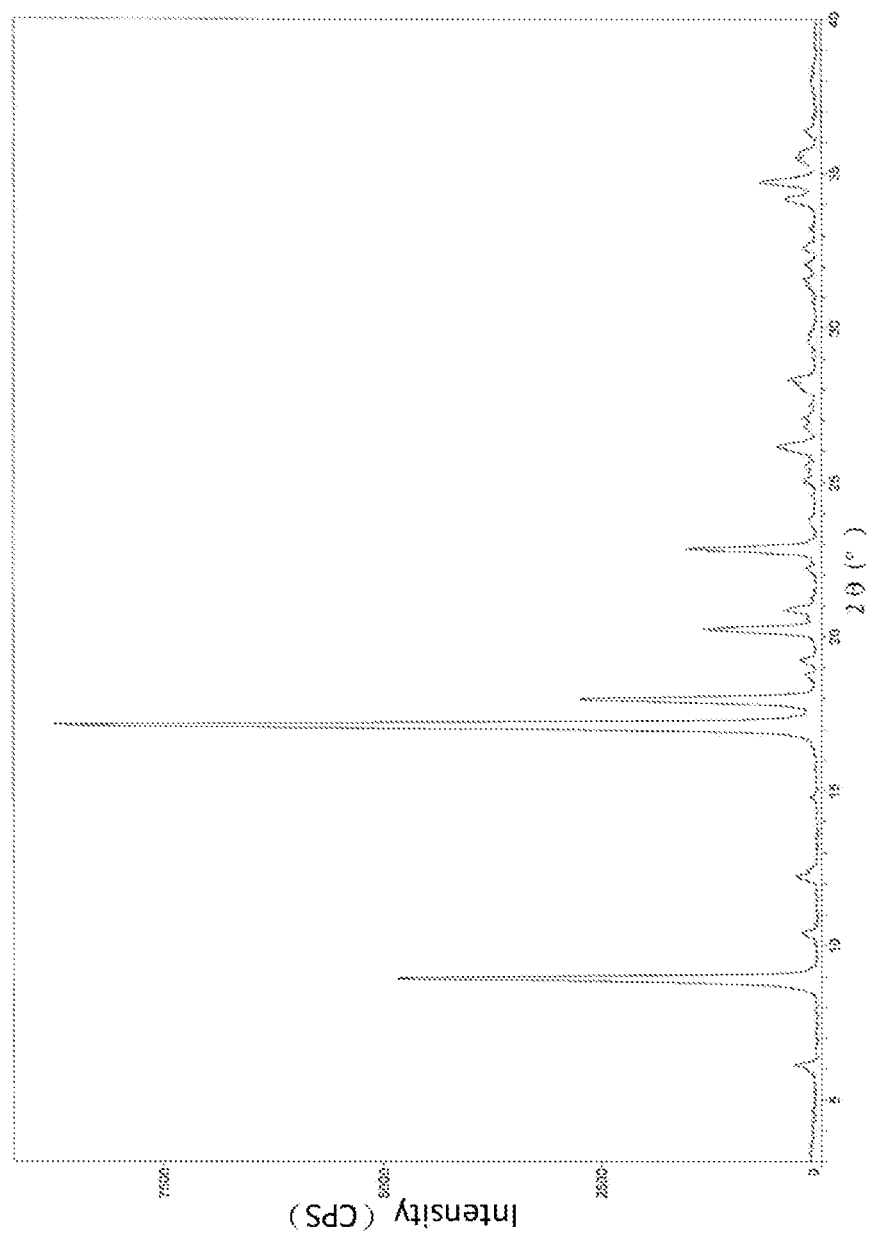
FIG. 1 is an X-ray powder diffraction pattern of crystal form I of fludarabine phosphate obtained in Example 1.
Figure 2:
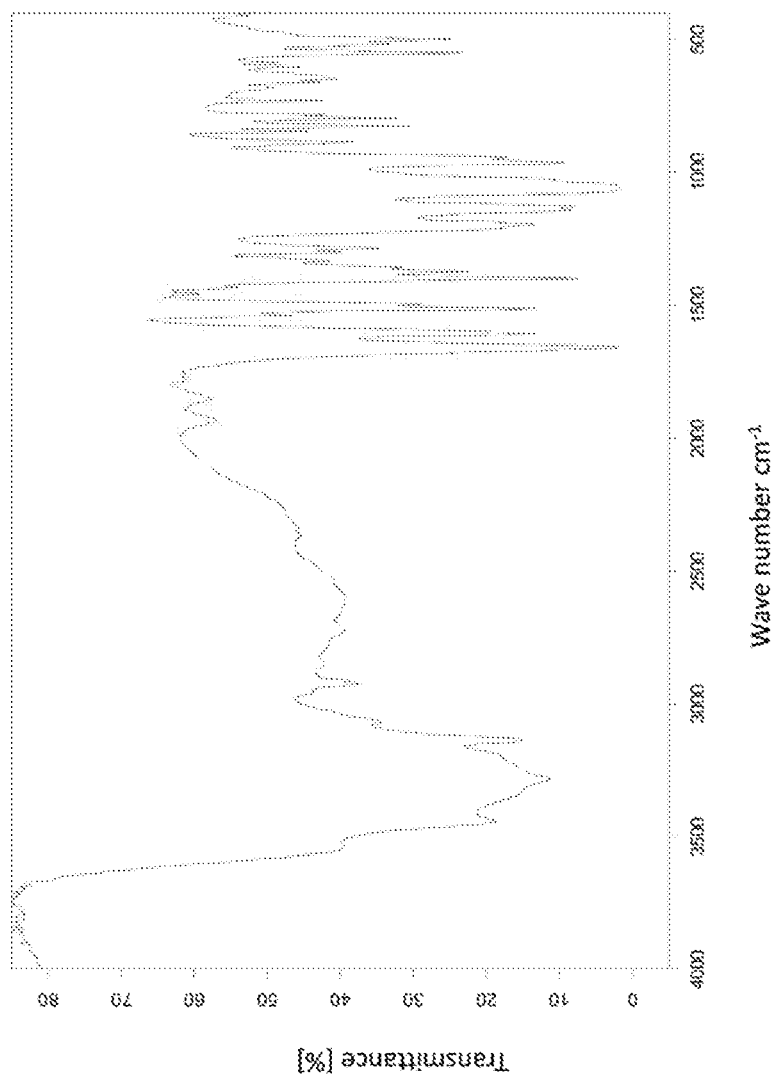
FIG. 2 is an infrared absorption spectrum of crystal form I of fludarabine phosphate obtained in Example 1.
Figure 3:
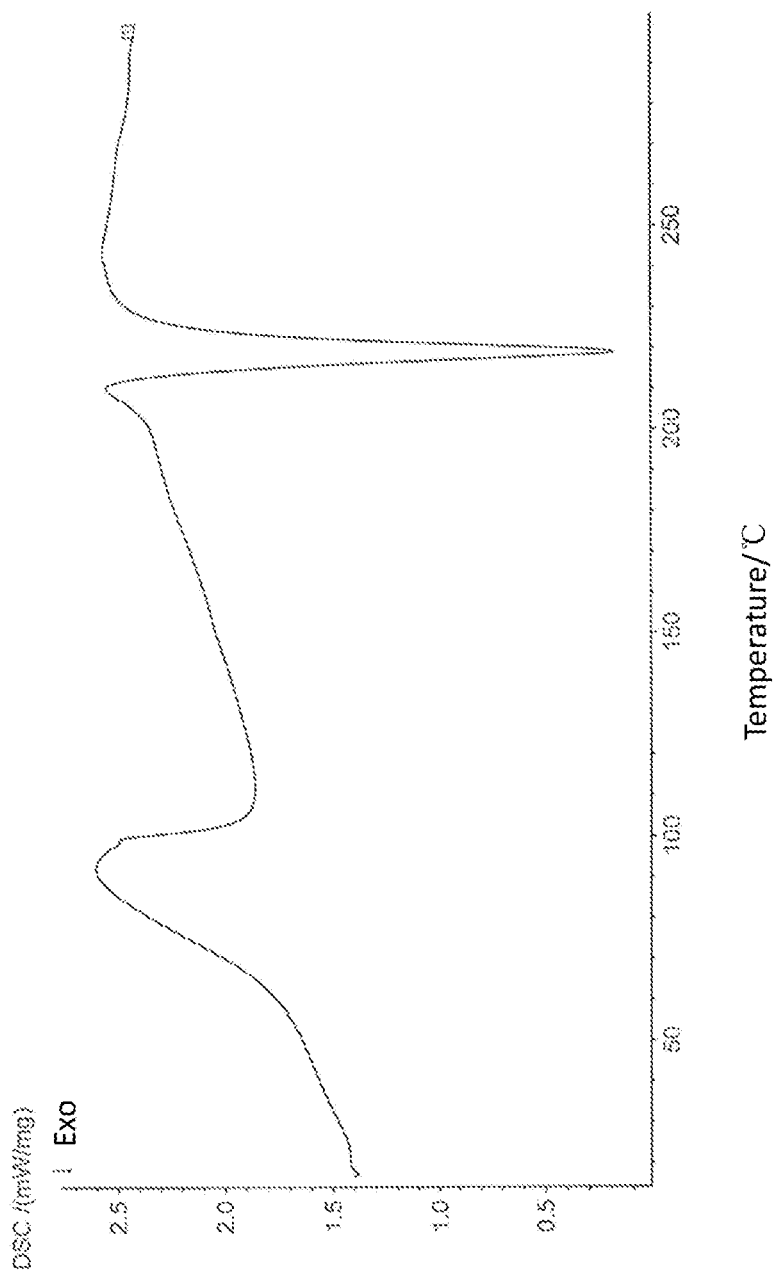
FIG. 3 is a DSC thermogram of crystal form I of fludarabine phosphate obtained in Example 1.
Figure 4:
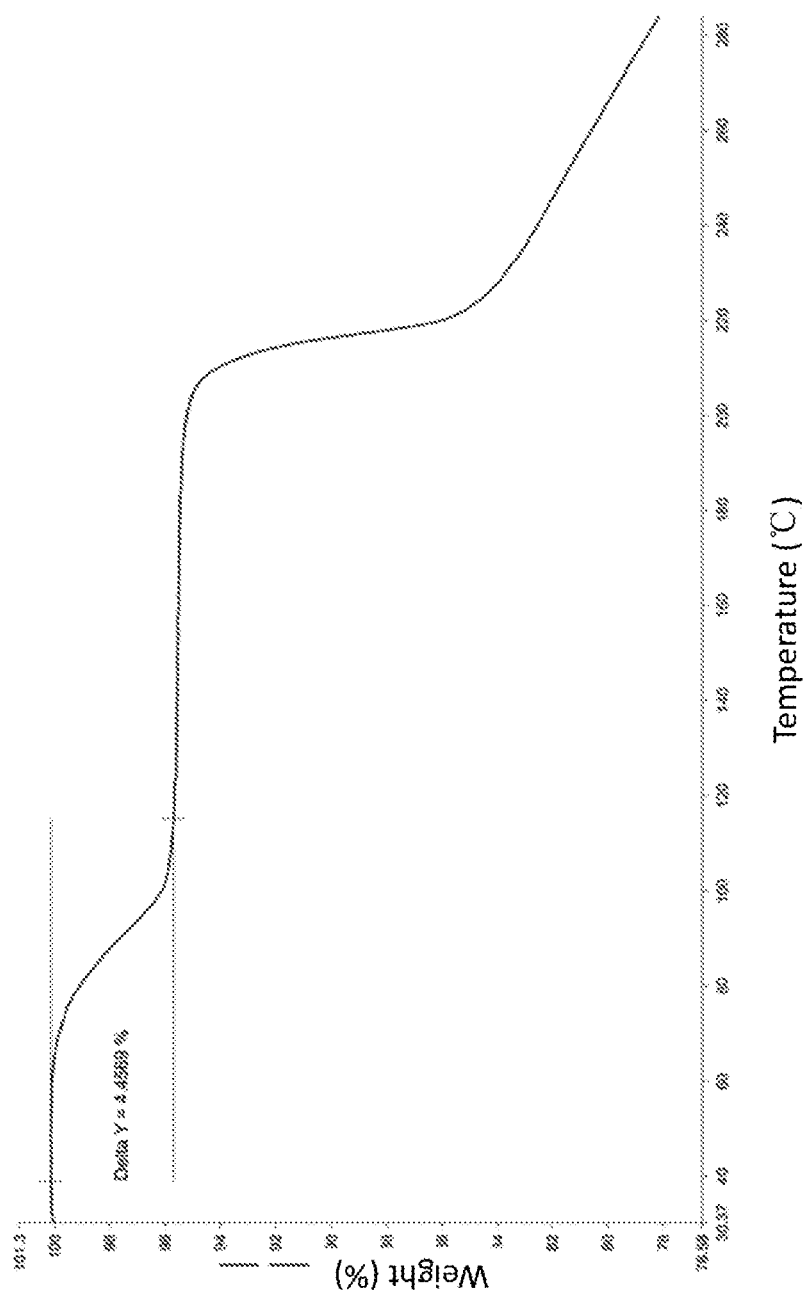
FIG. 4 is a TGA thermogram of crystal form I of fludarabine phosphate obtained in Example 1.

The X-ray powder diffraction pattern, the infrared spectrum, the DSC thermogram and the TGA thermogram of crystal form I can be seen in FIGS. 1-4 for details.

Example 2

10 g of fludarabine phosphate (HPLC purity>90%) was dissolved in 150 ml of aqueous hydrochloric acid solution, the temperature was controlled at 15-20° C., stirred continuously for 30 min, fludarabine phosphate was dissolved and obtain a solution of fludarabine phosphate; the solution was filtered and get clarified filtrate, saturated sodium hydroxide solution was added dropwise, pH=0.5, and crystallization was carried out under 25° C. while stirring for 8 h, the solution was filtered and dried under vacuum at 20° C., 6.1 g crystals were obtained, the purity was 99.2% by HPLC, the crystals were confirmed to be crystal form I by X-ray powder diffraction detection.

Example 3

10 g of fludarabine phosphate (HPLC purity>90%) was dissolved in 500 ml of aqueous hydrochloric acid solution, the temperature was controlled at 25-30° C., stirred continuously for 30 min, fludarabine phosphate was dissolved and obtain a solution of fludarabine phosphate; the solution was filtered and get clarified filtrate, saturated sodium hydroxide solution was added dropwise, pH=0, and crystallization was carried out under 25° C. while stirring for 8 h, the solution was filtered and dried under vacuum at 20° C., 4.5 g crystals were obtained, the purity was 99.6% by HPLC, the crystals were confirmed to be crystal form I by X-ray powder diffraction detection.

Example 4

10 g of fludarabine phosphate (HPLC purity>90%) was dissolved in 150 ml of aqueous sodium hydroxide solution, the temperature was controlled at 10-15° C., stirred continuously for 30 min, fludarabine phosphate was dissolved and obtain a solution of fludarabine phosphate; the solution was filtered and get clarified filtrate, concentrated hydrochloric acid solution was added dropwise, pH=1.0, and crystallization was carried out under 25° C. while stirring for 8 h, the solution was filtered and dried under vacuum at 20° C., 7.5 g crystals were obtained, the purity was 99.8% by HPLC, the crystals were confirmed to be crystal form I by X-ray powder diffraction pattern (XRPD).

Example 5

10 g of fludarabine phosphate (HPLC purity>90%) was dissolved in 300 ml of aqueous sodium hydroxide solution, the temperature was controlled at 15-20° C., stirred continuously for 30 min, fludarabine phosphate was dissolved and obtain a solution of fludarabine phosphate; the solution was filtered and get clarified filtrate, concentrated hydrochloric acid solution was added dropwise, pH=0.5, and crystallization was carried out under 25° C. while stirring for 7 h, the solution was filtered and dried under vacuum at 20° C., 6.2 g crystals were obtained, the purity was 99.5% by HPLC, the crystals were confirmed to be crystal form I by X-ray powder diffraction pattern (XRPD).

Example 6

10 g of fludarabine phosphate (HPLC purity>90%) was dissolved in 500 ml of aqueous sodium hydroxide solution, the temperature was controlled at 25-30° C., stirred continuously for 30 min, fludarabine phosphate was dissolved and obtain a solution of fludarabine phosphate; the solution was filtered and get clarified filtrate, concentrated hydrochloric acid solution was added dropwise, pH=0, and crystallization was carried out under 25° C. while stirring for 7 h, the solution was filtered and dried under vacuum at 20° C., 5.6 g crystals were obtained, the purity was 99.2% by HPLC, the crystals were confirmed to be crystal form I by X-ray powder diffraction pattern (XRPD).

Example 7

100 ml of the fermentation broth containing fludarabine phosphate (pH=7.0) was filtered (about 50 g/L), the filtrate was added to a crystallizer. The pH was adjusted to 1.0 with concentrated hydrochloric acid solution, crystallized for 8 h and filtered, 3.6 g crystals were obtained, HPLC-99.5%, the crystals were confirmed to be crystal form I by X-ray powder diffraction pattern (XRPD).

Example 8

100 ml of the fermentation broth containing fludarabine phosphate (pH=7.5) was filtered (about 50 g/L), the filtrate was added to a crystallizer. The pH was adjusted to 0.5 with concentrated hydrochloric acid solution, crystallized for 8 h and filtered, 3.8 g crystals were obtained, HPLC-99.6%, the crystals were confirmed to be crystal form I by X-ray powder diffraction pattern (XRPD).

Example 9

100 ml of the fermentation broth containing fludarabine phosphate (pH=7.3) was filtered (about 50 g/L), the filtrate was added to a crystallizer. The pH was adjusted to 0 with concentrated hydrochloric acid solution, crystallized for 8 h and filtered, 3.5 g crystals were obtained, HPLC-99.3%, the crystals were confirmed to be crystal form I by X-ray powder diffraction pattern (XRPD).

The X-ray powder diffraction patterns of the products obtained in Examples 2 to 9 are the same as that of Example 1 and will not be repeatedly shown here.

Example 10

10 g of fludarabine phosphate (HPLC purity>90%) was dissolved in 200 ml of aqueous hydrochloric acid solution, the temperature was controlled at 10-15° C., stirred continuously for 30 min, fludarabine phosphate was dissolved and obtain a solution of fludarabine phosphate; the solution was filtered and get clarified filtrate, saturated sodium hydroxide solution was added dropwise, pH=1.2, and crystallization was carried out under 25° C. while stirring for 8 h, the solution was filtered and the obtained solid was added into 10 ml of water and stirred for 4 h, filtered and dried under vacuum at 20° C., 5.3 g crystals were obtained, the purity was 99.2% by HPLC, the crystals were confirmed to be crystal form II by X-ray powder diffraction detection.

Figure 5:
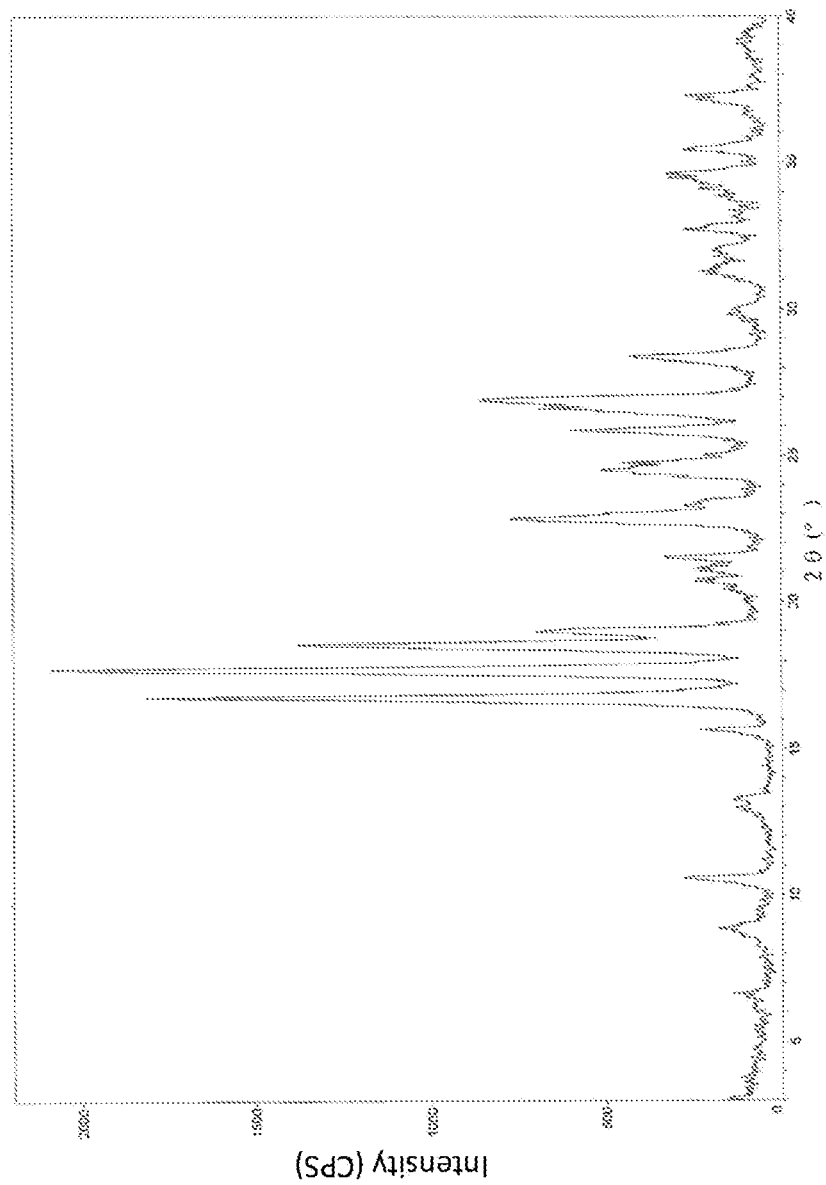
FIG. 5 is an X-ray powder diffraction pattern of crystal form II of fludarabine phosphate obtained in Example 10.
Figure 6:
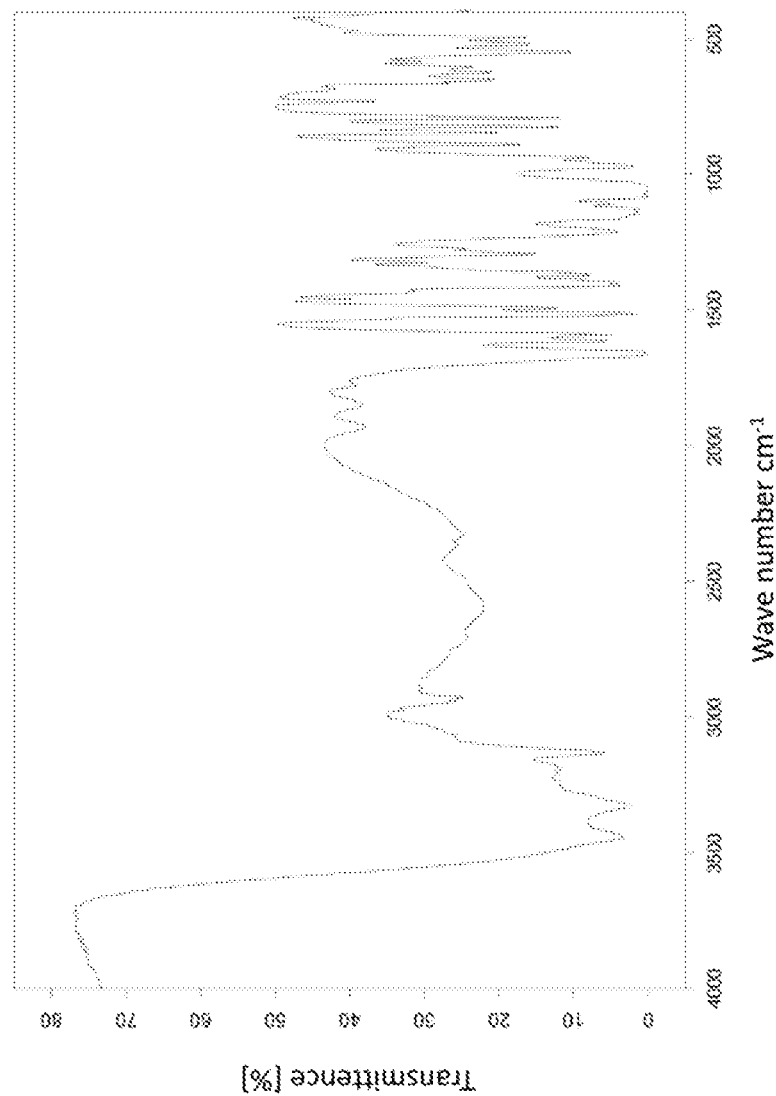
FIG. 6 is an infrared absorption spectrum of crystal form II of fludarabine phosphate obtained in Example 10.
Figure 7:
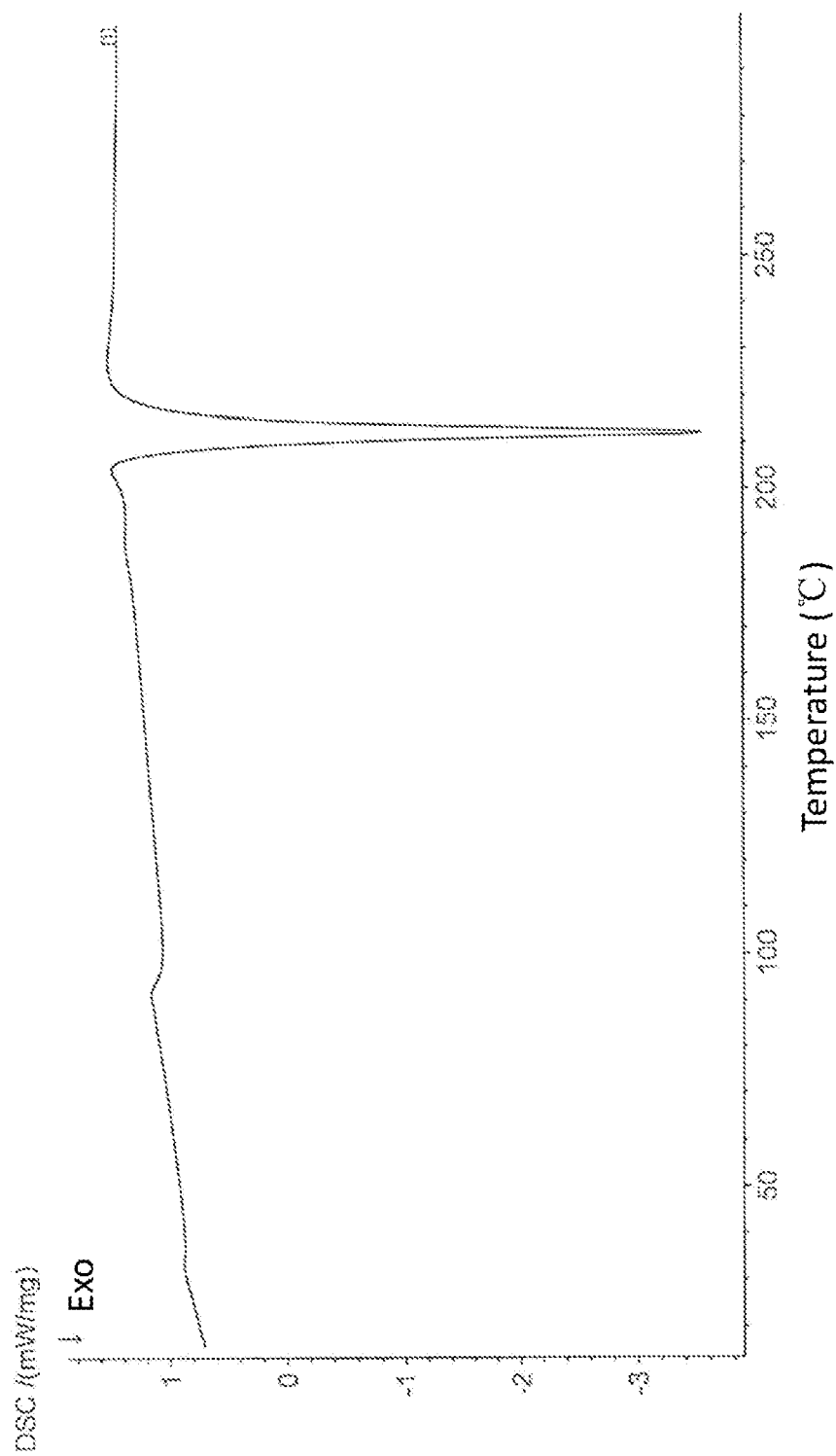
FIG. 7 is a DSC thermogram of crystal form II of fludarabine phosphate obtained in Example 10.
Figure 8:
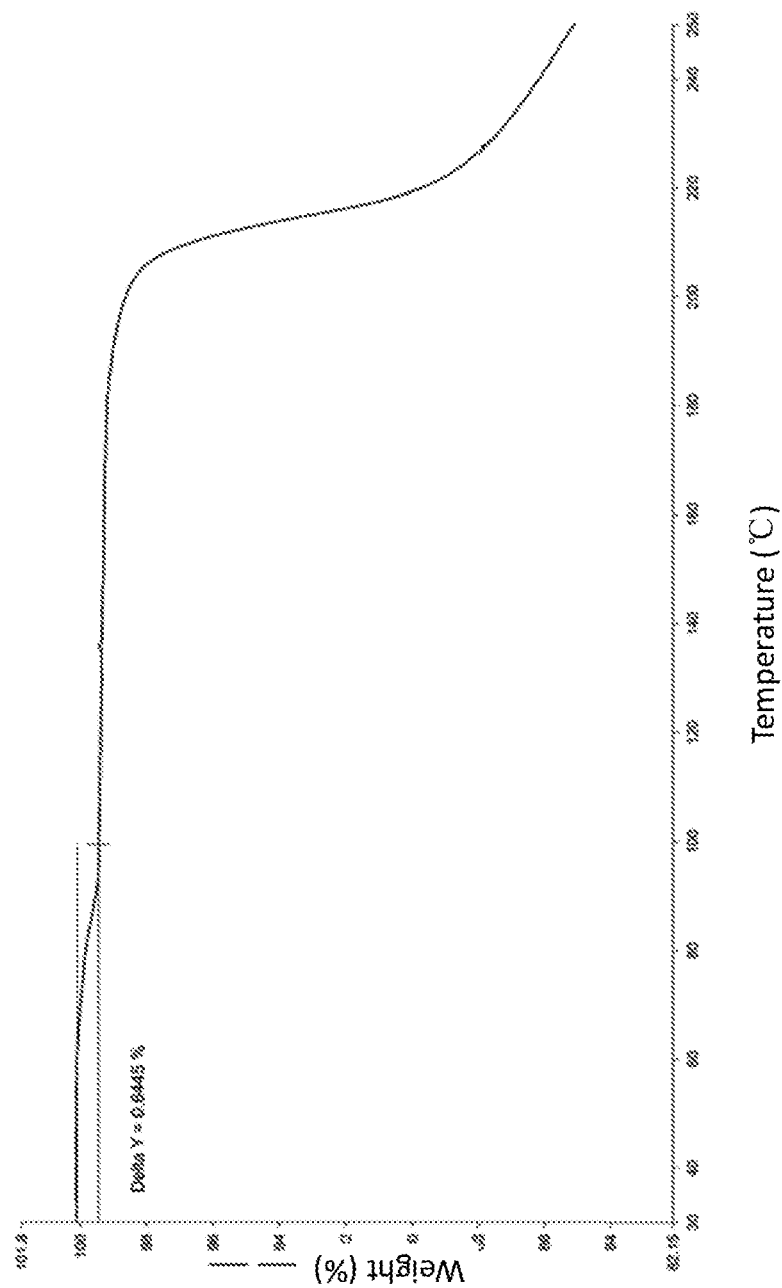
FIG. 8 is a TGA thermogram of crystal form II of fludarabine phosphate obtained in Example 10.

The X-ray powder diffraction pattern, the infrared spectrum, the DSC thermogram and the TGA thermogram of crystal form II can be seen in FIGS. 5-8 for details.

Example 11

10 g of fludarabine phosphate (HPLC purity>90%) was dissolved in 200 ml of aqueous hydrochloric acid solution, the temperature was controlled at 15-20° C., stirred continuously for 30 min, fludarabine phosphate was dissolved and obtain a solution of fludarabine phosphate; the solution was filtered and get clarified filtrate, saturated sodium hydroxide solution was added dropwise, pH=1.5, and crystallization was carried out under 25° C. while stirring for 8 h, the solution was filtered and the obtained solid was added into 10 ml of water and stirred for 4 h, filtered and dried under vacuum at 20° C., 4.8 g crystals were obtained, the purity was 99.2% by HPLC, the crystals were confirmed to be crystal form II by X-ray powder diffraction pattern (XRPD).

Example 12

10 g of fludarabine phosphate (HPLC purity>90%) was dissolved in 200 ml of aqueous hydrochloric acid solution, the temperature was controlled at 15-20° C., stirred continuously for 30 min, fludarabine phosphate was dissolved and obtain a solution of fludarabine phosphate; the solution was filtered and get clarified filtrate, saturated sodium hydroxide solution was added dropwise, pH=2.0, and crystallization was carried out under 25° C. while stirring for 8 h, the solution was filtered, and the obtained solid was added into 10 ml of water and stirred for 4 h, filtered and dried under vacuum at 20° C., 5.3 g crystals were obtained, the purity was 99.3% by HPLC, the crystals were confirmed to be crystal form II by X-ray powder diffraction pattern (XRPD).

Example 13

10 g of fludarabine phosphate (HPLC purity>90%) was dissolved in 200 ml of aqueous sodium hydroxide solution, the temperature was controlled at 25-30° C., stirred continuously for 30 min, fludarabine phosphate was dissolved and obtain a solution of fludarabine phosphate; the solution was filtered and get clarified filtrate, concentrated hydrochloric acid solution was added dropwise, pH=2.0, and crystallization was carried out under 25° C. while stirring for 8 h, the solution was filtered and the obtained solid was added into 10 ml of water and stirred for 4 h, filtered and dried under vacuum at 20° C., 5.6 g crystals were obtained, the purity was 99.1% by HPLC, the crystals were confirmed to be crystal form II by X-ray powder diffraction pattern (XRPD).

Example 14

10 g of fludarabine phosphate (HPLC purity>90%) was dissolved in 200 ml of aqueous sodium hydroxide solution, the temperature was controlled at 25-30° C., stirred continuously for 30 min, fludarabine phosphate was dissolved and obtain a solution of fludarabine phosphate; the solution was filtered and get clarified filtrate, concentrated hydrochloric acid solution was added dropwise, pH=1.5, and crystallization was carried out under 25° C. while stirring for 8 h, the solution was filtered and the obtained solid was added into 10 ml of water and stirred for 4 h, filtered and dried under vacuum at 20° C., 4.9 g crystals were obtained, the purity was 99.2% by HPLC, the crystals were confirmed to be crystal form II by X-ray powder diffraction pattern (XRPD).

Example 15

10 g of fludarabine phosphate (HPLC purity>90%) was dissolved in 200 ml of aqueous sodium hydroxide solution, the temperature was controlled at 25-30° C., stirred continuously for 30 min, fludarabine phosphate was dissolved and obtain a solution of fludarabine phosphate; the solution was filtered and get clarified filtrate, concentrated hydrochloric acid solution was added dropwise, pH=1.2, and crystallization was carried out under 25° C. while stirring for 8 h, the solution was filtered and the obtained solid was added into 10 ml of water and stirred for 4 h, filtered and dried under vacuum at 20° C., 4.3 g crystals were obtained, the purity was 99.3% by HPLC, the crystals were confirmed to be crystal form II by X-ray powder diffraction pattern (XRPD).

The X-ray powder diffraction patterns of the products obtained in Examples 11 to 15 are the same as that of Example 10 and will not be repeatedly shown here.

Tests of Dissolution Rates for Crystal Form I and Crystal Form II of Fludarabine Phosphate

TABLE 3

| Samples | Time | Reading | Turbidity | Solution state |
|---|---|---|---|---|
| Purified water | — | 0.00 | <0.5 | Clear |
| Crystal form I | 5 s | 2.2 | 1 > Sample > 0.5 | Clear |
| | 10 s | 1.75 | 1 > Sample > 0.5 | Clear |
| | 20 s | 1.75 | 1 > Sample > 0.5 | Clear |
| | 30 s | 1.75 | 1 > Sample > 0.5 | Clear |
| | 40 s | 1.75 | 1 > Sample > 0.5 | Clear |
| | 50 s | 1.75 | 1 > Sample > 0.5 | Clear |
| | 60 s | 1.75 | 1 > Sample > 0.5 | Clear |
| | 70 s | 1.75 | 1 > Sample > 0.5 | Clear |
| | 80 s | 1.75 | 1 > Sample > 0.5 | Clear |
| | 90 s | 1.75 | 1 > Sample > 0.5 | Clear |
| | 100 s | 1.75 | 1 > Sample > 0.5 | Clear |
| Cyrstal form II | 5 s | None | Sample >1 | Turbid |
| | 10 s | None | Sample >1 | Turbid |
| | 20 s | None | 1 > Sample > 0.5 | Turbid |
| | 30 s | None | 1 > Sample > 0.5 | Turbid |
| | 40 s | 6.41 | 1 > Sample > 0.5 | Turbid |
| | 50 s | 4.54 | 1 > Sample > 0.5 | A small amount of solids were not dissolved |
| | 60 s | 3.32 | 1 > Sample > 0.5 | A small amount of solids were not dissolved |
| | 70 s | 2.56 | 1 > Sample > 0.5 | Clear |
| | 80 s | 2.41 | 1 > Sample > 0.5 | Clear |
| | 90 s | 2.29 | 1 > Sample > 0.5 | Clear |
| | 100 s | 2.29 | 1 > Sample > 0.5 | Clear |

From the results of Table 3, it can be seen that crystal form I and crystal form I of fludarabine phosphate of the present invention all have better solubility in purified water, and also have better dissolution rates and chemical stabilities. In a short period of time, good clarity can be achieved for both crystal form I and crystal form II of fludarabine phosphate of the present invention. Among them, crystal form I of fludarabine phosphate of the present invention is more preferable.

Stability Tests for Crystal Form I and Crystal Form II of Fludarabine Phosphate

Packaging condition: crystal form I and crystal form II of fludarabine phosphate were first sealed and packaged with PE bags respectively, and then sealed and packaged with aluminum foil bags outside, the samples were reserved at room temperature and refrigerated conditions, the samples were tested with the liquid chromatography. The test condition of the liquid chromatography is described in SUMMARY OF THE INVENTION section of this application.

TABLE 4

|  | Crystal form II | | Crystal form I | |
| --- | --- | --- | --- | --- |
|  | Room temperature | Refrigerated | Room temperature | Refrigerated |
| Before the samples were reserved | 99.677% | | 99.685% | |
| The samples were reserved for one month | 99.673% | 99.677% | 99.685% | 99.685% |
| The samples were reserved for two months | 99.668% | 99.677% | 99.685% | 99.685% |
| The samples were reserved for three months | 99.667% | 99.677% | 99.685% | 99.685% |
| The samples were reserved for four months | 99.663% | 99.677% | 99.684% | 99.685% |
| The samples were reserved for five months | 99.663% | 99.677% | 99.684% | 99.685% |
| The samples were reserved for six months | 99.663% | 99.677% | 99.684% | 99.685% |

Note:
room temperature corresponds to 10-30° C. prescribed in "Pharmacopoeia",
refrigerated corresponds to 2-10° C. prescribed in "Pharmacopoeia", humidity is 75%.

From the results of Table 4, it can be seen that crystal form I and crystal form II of fludarabine phosphate of the present invention all have good stabilities under room temperature and refrigerated conditions, and crystal form I and crystal form II of fludarabine phosphate of the present invention are more stable under refrigerated condition.

The invention claimed is:

1. A crystal form I of 9-β-D-arabinofuranosyl-2-fluoroadenine-5'-phosphate, wherein the X-ray powder diffraction pattern thereof has characteristic peaks at 2θ(°) values of 9.1±0.2, 17.3±0.2, 18.1±0.2, 20.4±0.2, 23.0±0.2, 28.1±0.2.

2. The crystal form I according to claim 1, wherein the X-ray powder diffraction pattern thereof has characteristic peaks at 2θ(°) values of 6.2±0.2, 10.5±0.2, 12.3±0.2, 18.9±0.2, 26.3±0.2.

3. A pharmaceutical composition comprising the crystal form I of 9-β-D-arabinofuranosyl-2-fluoroadenine-5'-phosphate according to claim 1.

4. A method for the treatment of a tumor in a subject, comprising providing the crystal form I of 9-β-D-arabinofuranosyl-2-fluoroadenine-5'-phosphate according to claim 1 to the subject.

5. A preparation method of the crystal form I of 9-β-D-arabinofuranosyl-2-fluoroadenine-5'-phosphate according to claim 1, wherein the method is selected from any one of the following methods:
method 1), comprising the following steps of:
(1) 9-β-D-arabinofuranosyl-2-fluoroadenine-5'-phosphate is added to an acidic aqueous solution;
(2) dissolved;
(3) the pH is adjusted with an alkaline solution, wherein the pH is less than 1.2;
(4) crystallized;
(5) filtered to obtain crystal form I of 9-β-D-arabinofuranosyl-2-fluoroadenine-5'-phosphate;
method 2), comprising the following steps of:
(1) 9-β-D-arabinofuranosyl-2-fluoroadenine-5'-phosphate is added to an alkaline aqueous solution;
(2) dissolved;
(3) the pH is adjusted with an acidic solution, wherein the pH is less than 1.2;
(4) crystallized;
(5) filtered to obtain crystal form I of 9-β-D-arabinofuranosyl-2-fluoroadenine-5'-phosphate;
method 3), comprising the following steps of:
(1) the fermentation broth containing 9-β-D-arabinofuranosyl-2-fluoroadenine-5'-phosphate is filtered;
(2) the filtrate is added to a crystallizer;
(3) the pH is adjusted with an acidic solution, wherein the pH is less than 1.2;
(4) crystallized;
(5) filtered to obtain crystal form I of 9-β-D-arabinofuranosyl-2-fluoroadenine-5'-phosphate.

6. The preparation method of the crystal form I of 9-β-D-arabinofuranosyl-2-fluoroadenine-5'-phosphate according to claim 5, wherein in
method 1), step (3), the pH is in the pH range of 0-1.0.

7. The preparation method of the crystal form I of 9-β-D-arabinofuranosyl-2-fluoroadenine-5'-phosphate according to claim 5, wherein in
method 2), step (3), the pH is in the pH range of 0-1.0.

8. The preparation method of the crystal form I of 9-β-D-arabinofuranosyl-2-fluoroadenine-5'-phosphate according to claim 5, wherein in
method 3), step (3), the pH is in the pH range of 0-1.0.

9. The preparation method according to claim 5, wherein the weight-to-volume ratio of 9-β-D-arabinofuranosyl-2-fluoroadenine-5'-phosphate to the solvent of method 1) or method 2) is 1:10-1:100 (g/ml).

10. The preparation method according to claim 9, wherein the weight-to-volume ratio of 9-β-D-arabinofuranosyl-2-fluoroadenine-5'-phosphate to the solvent of method 1) or method 2) is 1:15-1:50 (g/ml).

* * * * *